United States Patent [19]

Evans et al.

[11] Patent Number: 4,882,271

[45] Date of Patent: Nov. 21, 1989

[54] PROCESS FOR PREPARATION OF HIGH MOLECULAR WEIGHT CELL-ASSOCIATED PROTEIN OF CAMPYLOBACTER PYLORI AND USE FOR SEROLOGICAL DETECTION OF CAMPYLOBACTER PYLORI INFECTION

[75] Inventors: Dolores G. Evans; Doyle J. Evans; David Y. Graham, all of Houston, Tex.

[73] Assignee: Baylor College of Medicine, Houston, Tex.

[21] Appl. No.: 166,138

[22] Filed: Mar. 10, 1988

[51] Int. Cl.$^4$ ............... G01N 33/53; G01N 33/543; C12Q 1/58; C07K 15/00

[52] U.S. Cl. .................................... 435/7; 435/12; 435/810; 436/501; 436/518; 436/808; 436/811; 436/813; 530/413; 530/350

[58] Field of Search ............ 435/7, 12, 174, 810; 436/501, 518, 527, 529, 531, 533, 547, 804, 808, 811, 813; 530/350, 413, 806, 810, 825

[56] References Cited

U.S. PATENT DOCUMENTS

| | | | |
|---|---|---|---|
| 4,529,602 | 7/1985 | Wada et al. | 514/569 |
| 4,748,113 | 5/1988 | Marshall | 435/12 |
| 4,785,086 | 11/1988 | Rashtchian et al. | 435/6 |

FOREIGN PATENT DOCUMENTS

| | | | |
|---|---|---|---|
| 0119556 | 9/1984 | European Pat. Off. | 436/548 |
| 0204438 | 12/1986 | European Pat. Off. | 435/12 |
| 8701119 | 2/1987 | PCT Int'l Appl. | 435/7 |

OTHER PUBLICATIONS

Graham et al., 88th Annual Meeting of the American Gastroenterological Association and Digestive Disease Week, Chicago, Ill., U.S.A., May 9-15, 1987, Gastroenterology, 92 (5 Part 2), p. 1411.

Evans et al., 87th Annual Meeting of the American Society for Microbiology, Atlanta, Ga., U.S.A., Mar. 1-6, 1987, Abstr Annu. Meet. Am. Soc. Microbiol., 87(O), p. 112.

Scand. J. Gastroenterol, Tyllstrom, J. et al., 19:755-760 (1984).

Hospital Practice, Marshall, B. J., Aug. 15, 1987, pp. 87-96.

American Journal of Gastroenterology, Graham, D. Y. and Klein, P. D. 82:283, 286 (1987).

Lancet, Graham, D. Y. et al., May 23, 1987, 1174-1177.

Journal of General Microbiology, Newell, D. G., 133:163-170 (1987).

Infection and Immunity, Perez-Perez, G. I. and Blazer, M. J., 55:1256-1263 (1987).

Gut, Rathbone, P. J. et al., 27:642-647 (1986).

The Medical Journal of Australia, Kaldor, J. et al., 145:133-135 (1986).

New Zealand Medical Journal, Morris, A. et al., 99:657-659 (1986).

The Journal of Infectious Diseases, Goodwin, C. Stewart et al., vol. 155, No. 3-Mar. 1987, pp. 488-494.

J. Clin Pathol Jones, D. M. et al.; 1984; 37:1002-1006.

J. Med. Microbiol., Jones, D. M. et al., vol. 22, (1986) 57-62.

Journal of Clinical Microbiology, von Wulffen, H. et al., Nov. 1986, pp. 716-720, vol. 24.

*Primary Examiner*—Robert J. Warden
*Assistant Examiner*—Florina B. Hoffer
*Attorney, Agent, or Firm*—Fulbright & Jaworski

[57] ABSTRACT

An antigen for the detection of *Compylobacter pylori* infections and an assay for the serological detection of *Campylobacter pylori*. The antigen includes high molecular weight cell-associated proteins purified from *Campylobacter pylori*. The antigen can be used in a variety of assays including radioimmunoassay, ELISA, latex agglutination, complement fixation, and indirect hemagglutination. Furthermore, the antigens can be combined with a solid support in kit form.

9 Claims, 4 Drawing Sheets

PROCESS FOR PREPARATION OF HIGH MOLECULAR WEIGHT CELL-ASSOCIATED PROTEIN OF CAMPYLOBACTER PYLORI AND USE FOR SEROLOGICAL DETECTION OF CAMPYLOBACTER PYLORI INFECTION

FIELD OF THE INVENTION

This invention relates to high molecular weight cell-associated proteins used as antigens for the detection of antibody to *Campylobacter pylori* infection. It is useful both for the preparation of the antigen as well as in the detection and monitoring of the infection.

BACKGROUND OF THE INVENTION

*Campylobacter pylori* (*C. pylori*) was first isolated in 1982. It is now known to be an important cause of gastritis and has been associated with duodenal ulcer, gastric ulcer, dyspepsia and gastric carcinoma. Since the discovery in 1982 there has been a tremendous worldwide interest in *C. pylori* and in trying to delineate its actual role in gastric disease and the formation of ulcers. Despite the numerous studies showing a close association between *C. pylori* and abnormal gastric pathology, there is insufficient evidence to determine conclusively whether the organism is pathogenic or opportunistic. Nevertheless, the presence of *C. pylori* is an important consideration in treating gastric disease.

Patients colonized with *C. pylori* elicit a specific antibody response which is potentially useful as a diagnostic aid and for monitoring the disease state during treatment. Consequently, many systems have been developed to detect serum anti *C. pylori* antibodies. However, preliminary studies suggest that *C. pylori* displays antigenic cross-reactivity with the thermophilic campylobacteria *C. jejuni* and *C. coli*. This cross-activity results in lack of specificity.

In attempts to avoid the problems associated with cross-reactivity, investigators have extensively studied the acid extractable surface proteins and outer membrane proteins of *C. pylori*. Newall, D. G., Journal of General Microbiology 133:163–170 (1987); and Perez-Perez, G. I. and Blaser, M. J., Infection and Immunity 55:1256–1263 (1987). Newall demonstrated that there existed acid extractable proteins in the molecular range of 20,000 to some of these proteins were similar to proteins of *C. jejuni* and many also showed cross-reactivity with *C. jejuni*. At least one major antigen (approximately 60,000 daltons) showed only minimum cross-reactivity with *C. jejuni*, however, there still was some cross-reactivity. On the other hand, Perez-Perez showed that an antigen of about 62,000 daltons had significant cross-reactivity. *C. pylori* is capable of eliciting both a systemic and local antibody response in patients with chronic gastritis, however, this secretory-antibody response does not appear to eliminate the colonization. Rathbone, B. J. et al., Gut, 27:642–647 (1986). Rathbone et al used the whole organism in their immunological assay.

Other studies using the immunoblot technique show that *C. pylori* has a number of immuno-reactive components in the range of 100,000 daltons or less. Kaldor, J. et al. The Medical Journal of Australia 145:133–135 (1986).

Whole organism ELISA assays detect *C. pylori* antibody but still are unable to solve the cross-reactivity problem. Morris et al. The New Zealand Medical Journal 99:657–659 (1986).

Acid-glycine extracts of *C. pylori* detect antibodies using ELISA techniques. However, a number of false positives and false negatives exist. Although the relative number of each false result can be regulated by adjusting the cut off point, there is still significant overlap between the groups. Goodwin et al. The Journal of Infectious Disease 155:488–494 (1987). Similar results are found using complement fixation, bacterial aglutination and immunoblotting. Jones et al. General Clinical Pathology 37:1002–1006 (1984) and Jones et al. J. of Ed. Microbiology 22:57–62 (1986). Acid washed fractions show similar results in both complement fixation and SDS-PAGE immunoblots. Wulffen et al. Journal of Clinical Microbiology 24:716–720 (1986).

Numerous reports exist showing *C. pylori* antibodies in the serum of affected humans. All of the studies have dealt with the outside surface of the microorganism. In these test systems, the antigen is either the whole organism or sub parts of the flaggella and outside membrane in the molecular weight range of about 100,000 daltons or less. None of these studies are adequate to allow accurate detection of the infection. There is significant misclassification, both false positive and false negative, as well as significant cross-reactivity with other organisms, such as *C. jejuni* and *C. coli*. Thus, there exists a need for a quick immunological method to specifically detect the *C. pylori* antibody. The present invention meets this need. The present invention describes a new and accurate serological assay for the diagnosis of *C. pylori* infection. Previously published results used lower molecular weight compounds and had significant levels of cross-reactivity with other bacteria. No other assay has the same overall reliability (sensitivity plus specificity).

The symptom dyspepsia is associated with large health care expenditures throughout the western world. Although accurate statistics as to the frequency of dyspepsia are difficult to obtain, recent studies have shown it to be a common problem. In England, for example, it has been estimated that approximately 1% of patients served by general practitioners will present each year with the primary complaint of dyspepsia. The costs of dyspepsia are many and include: (i) those for drugs such as antacids or $H_2$-receptor antagonists (sales of cimetidine and ranitidine were more than 2 billion dollars); (ii) charges for diagnostic evaluations such as barium upper gastrointestinal series or fiberoptic endoscopy and (iii) costs associated with time off from work. The effects of dyspepsia on drug use were studied by evaluating patients in Sweden in whom a clinical diagnosis of gastritis or non-ulcer dyspepsia was made. Tyllstrom et al. Scand. J Gastroenterol 1984, 19:755–60.

Tyllstrom found that antacid or $H_2$-receptor antagonist therapy was common among these patients. In fact, most patients who visited a physician were given a prescription. This result is similar to data from Britain in which 91% of such patients reported regular use of antacids. Tyllstrom calculated that 1% of the entire population of Sweden was taking a daily dose and that non-ulcer dyspepsia was a primary indication for cimetidine use, accounting for 35% of the prescriptions. There was also noted an increasing trend in the percentage of patients treated with cimetidine.

Because of the high incidence and cost of gastric problems and ulcers in western society, the ability to detect and monitor the treatment of these diseases is highly desirable. Thus the present invention is important in its ability to specifically detect *C. pylori* which is associated with these diseases and whose disappearance is associated with clinical improvement.

SUMMARY OF THE INVENTION

An object of the present invention is the isolation and purification of antigens from the high molecular weight cell-associated proteins of *C. pylori*.

An additional object of the present invention is a method for detecting *C. pylori* infection in humans.

A further object of the present invention is a diagnostic kit.

Thus, in accomplishing the foregoing objects, there is provided in accordance with one aspect of the present invention antigens from the high molecular weight cell-associated proteins (HM-CAP) of *C. pylori*, the antigens in substantially purified form having a molecular weight of about 300,000 to 700,000 daltons, a PI on isoelectric focusing of about 5.9 to 6.3, being soluble in phosphate-buffered saline and tris-chloride buffers. In one preferred embodiment the antigen demonstrates urease activity.

Another embodiment includes a serological assay for the detection of *C. pylori* infection in humans comprising combining the antigens isolated from HM-CAP with a serum sample to be tested according to the immulogical method selected from the group consisting of enzyme-linked immunosorbent assay, radioimmuno assay, complement fixation, latex agglutination, and passive hemagglutination test using HM-CAP coated erythrocytes pre-treated (activated) by glutaraldehyde or tannic acid.

In one embodiment an enzyme-linked immunosorbent assay is used. This assay includes immobilizing the antigen on a solid phase support, adding serum sample to the immobilized antigen, incubating the serum sample and the immobilized antigen to form an antigen-antibody complex. Adding an enzyme-conjugated anti-human IgG to the antigen-antibody complex and incubating to form an antigen-antibody enzyme-conjugated anti-human IgG complex. In a preferred embodiment the enzyme can include alkaline phosphatase, horseradish peroxidase or beta-galactosidase. When alkaline phosphatase is used, para-nitrophenyl phosphate (enzyme substrate) is added to the complex. This substrate reacts with the alkaline phosphatase yielding a color which can be measured to determine the amount of antibody.

Another embodiment includes a kit which is comprised of the antigens of high molecular weight cell-associated proteins of *C. pylori* immobilized on a solid phase support.

Other and further objects, features and advantages will be apparent from the following description of the presently preferred embodiments of the invention given for the purpose of disclosure when taken in conjunction with the accompanying drawings.

BRIEF DESCRIPTION OF THE DRAWINGS

The invention will be more readily understood from a reading of the following specification and by reference to the accompanying drawings, forming a part thereof, where examples of embodiments of the invention are shown and wherein.

DETAILED DESCRIPTION

The drawings are not necessarily to scale and certain features of the invention may be exaggerated in scale or shown in schematic form in the interest of clarity and conciseness. It will be readily apparent to one skilled in the art that various substitutions and modifications may be made to the invention disclosed herein without departing from the scope and spirit of the invention.

Antigens from the high molecular weight cell-associated proteins (HM-CAP) of *C. pylori* are in substantially purified form having a molecular weight of about 300,000 to 700,000 daltons, a PI on isoelectric focusing of about 5.9 to 6.3, being soluble in commonly used buffered solutions including PBS (phosphate-buffered saline including about 0.05M phosphate buffer, about 0.85% NaCl at about pH 7.2) or Tris-chloride buffer (about 0.05M Tris, pH about 8.0). The protein components are detectable by absorption at 280 nm, lowering protein assay and by staining gels with Coomasee Blue. HM-CAP is extracted (solubilized) by treatment of *C. pylori* cells with n-octyl-glucoside (NOG). NOG extracts membrane and surface proteins without breaking the cells. In the preferred embodiment these antigens demonstrate urease activity.

When *C. pylori* cells are harvested and washed, urease activity remains bound to the bacterial cells. After sonication and centrifugation urease enzyme activity resides in the pellet providing further evidence that the protein with urease activity is associated with the outer surface of the membrane. The "proteins associated with the outer surface of the membrane" refers to proteins which are either in the membrane or are on the surface of the membrane. Furthermore, disruption of the cell surface without breaking the cell releases urease activity into the supernatant fraction.

The antigens can be prepared by a variety of methods. In the preferred embodiment, *C. pylori* is first grown on blood agar plates. The blood agar plates are prepared with about 7% fresh (not more than eight days old) horse blood and DIFCO brain-heart fusion base. After incubating the cultures for about 48 hours at about 37° C. in about 12% $CO_2$ and about 100% humid atmosphere, the *C. pylori* are harvested from the plates. The harvested bacteria are washed with PBS centrifuged at about 8,000 rpm for about 12 minutes. This is repeated at least twice.

In another embodiment the *C. pylori* are grown in a broth medium composed of DIFCO brain-heart infusion broth containing about 10% horse serum, about 0.03% purified rabbit hemoglobin and about 0.15% DIFCO yeast extract. For broth cultures, the inoculum is prepared from a blood agar plate (as described above). Incubation conditions are the same as for blood agar plate cultures. Bacteria from broth are harvested by centrifugation at about 8,000 rpm for about 12 minutes and then the washing procedure as described for plate-grown bacteria is followed.

Next, the washed C. pylori cells, whether from broth or agar plates, are extracted by resuspending the washed bacteria in about 1% solution of n-octyl-glucoside in PBS, about pH 7.2, using about 2.5 ml per 1.0 ml of packed cells. After extraction for 20 minutes at room temperature the extraction suspension is centrifuged at about 15,000 rpm for 15 minutes. The supernatant is removed and dialyzed for 18 to 24 hours against 1,600 volumes (about 4 liters) against one-half concentration PBS containing 0.024% sodium azide as a preservative. The dialysate is centrifuged at about 18,000 rpm for about 15 minutes. The pellet material is discarded and the supernatant is saved. The supernatant contains the crude (HM-CAP). The crude HM-CAP preparation is placed on a Agarose A-5 m column and eluted with about 0.05M Tris-Cl buffer, at about pH 8.0 containing about 0.025% sodium azide. The column is about a 1.6 by 100 centimeter column. Approximately 2.5 milliliter fractions from the column are collected and monitored. The optical density of these fractions is determined at 280 nm and urease activity determined by assay with urea as substrate. The fractions (about 6 to 8) which contain maximum urease activity are pooled. These fractions which are pooled represent the molecular weight range of about 300,000 to 700,000 daltons. The HM-CAP preparation at this point contains at least two separate proteins.

Figure 1:
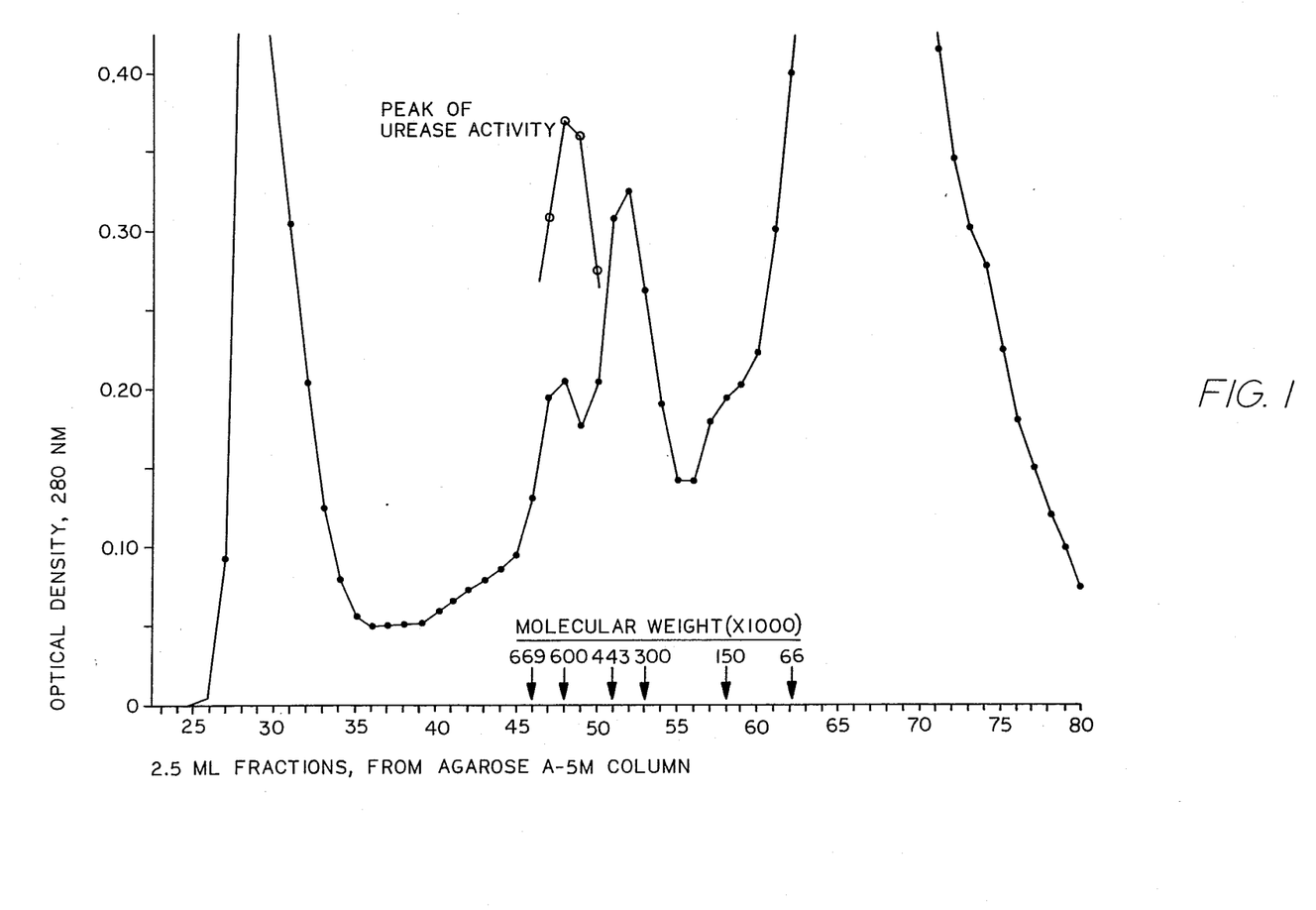
FIG. 1 is a typical elution profile of crude HM-CAP applied to an agarose A-5m column.

FIG. 1 shows the results obtained when 2.5 ml of the crude HM-CAP preparation is passed through an agarose A-5 m column. The peak of 280 nm absorbing material at fractions 47–49 coincides with the peak of urease activity and is closely followed by another peak of 280 nm absorbing material of lower molecular weight at fractions 51–52. These two peaks have considerable overlap and the partially purified HM-CAP, fractions 47–49, contains at least two and probably more molecular species. Further separations can be undertaken to separate these individual proteins.

Molecular weight (MW) was determined by eluting proteins of known molecular weights through the same agarose A-5m column and noting their elution positions, for example, thyroglobulin (MW 669,000) at fraction 46; aproferritin (MW 443,000) at fraction 51; yeast alcohol dehydrogenase (MW 150,000) at fraction 55; and bovine serum albumin (MW 66,000) at fraction 62. From these protein standards it is can be calculated that partially purified HM-CAP contains molecular species in the range of 300,000 (fraction 53) to 700,000 (fraction 46) molecular weight.

Figure 2:
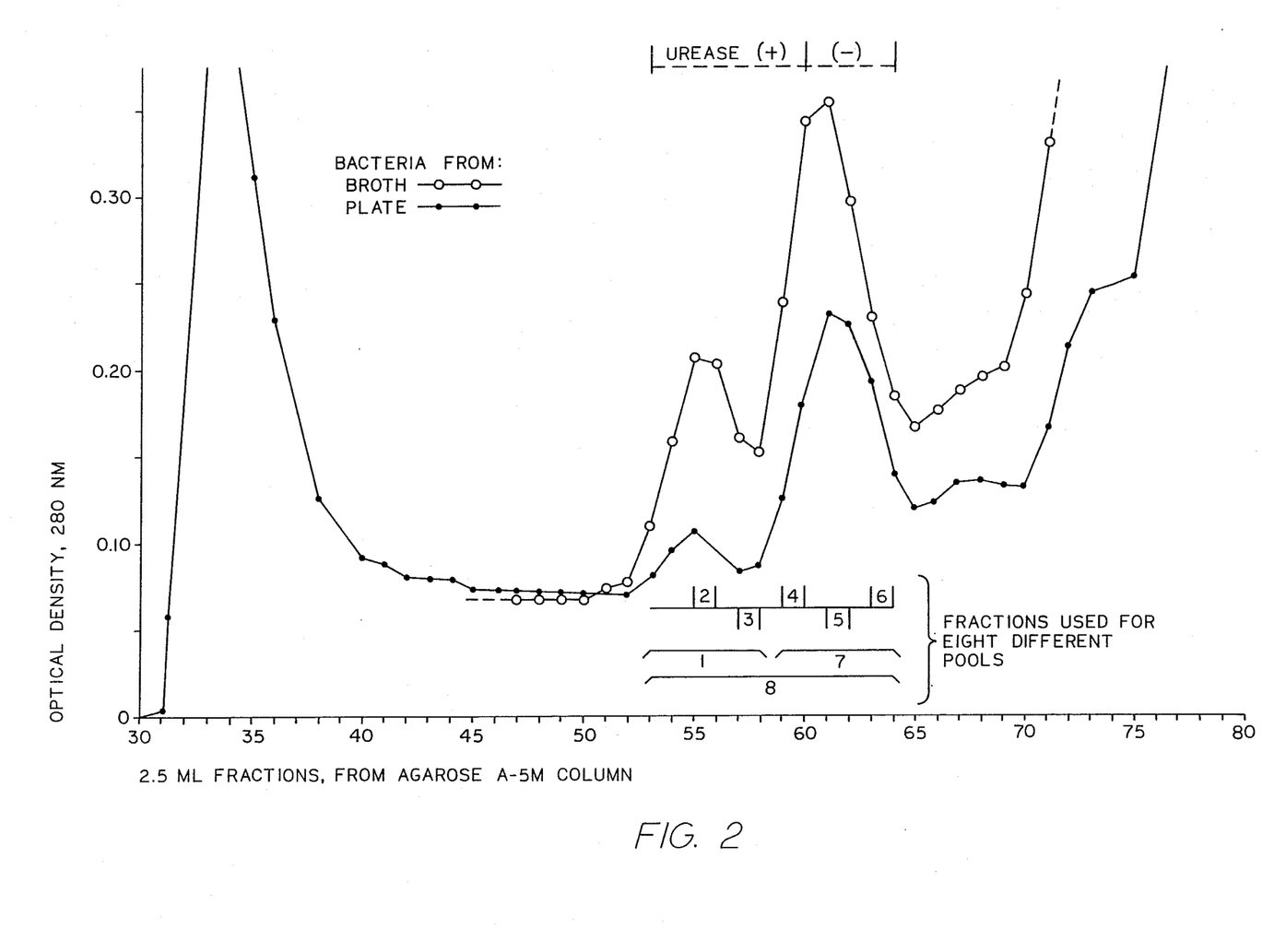
FIG. 2 is a typical elution profile of HM-CAP preparation from Broth and plate grown bacteria showing the region of urease activity.
Figure 3:
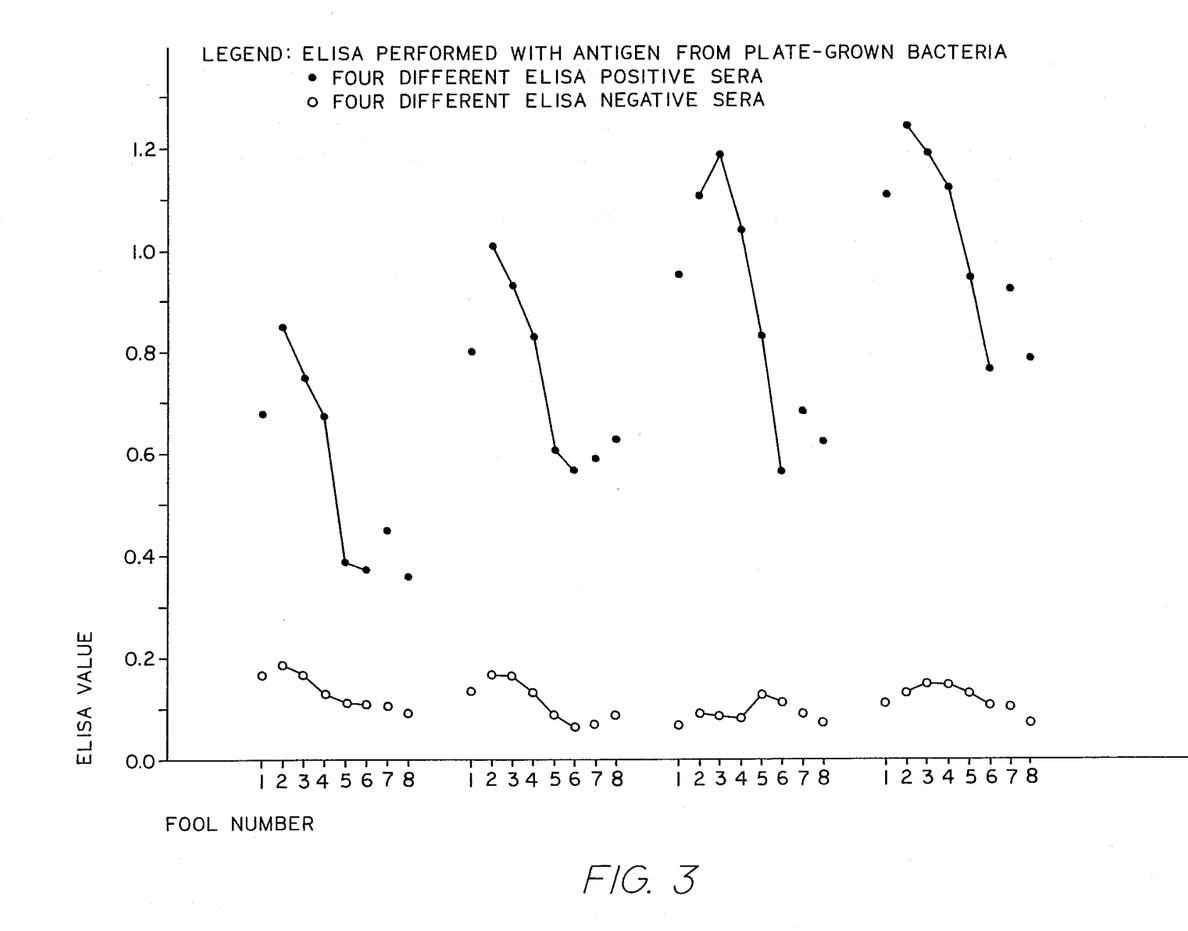
FIG. 3 compares four different positive and negative sera using an ELISA assay with antigen from plate grown bacteria to detect anti-*C. pylori*.
Figure 4:
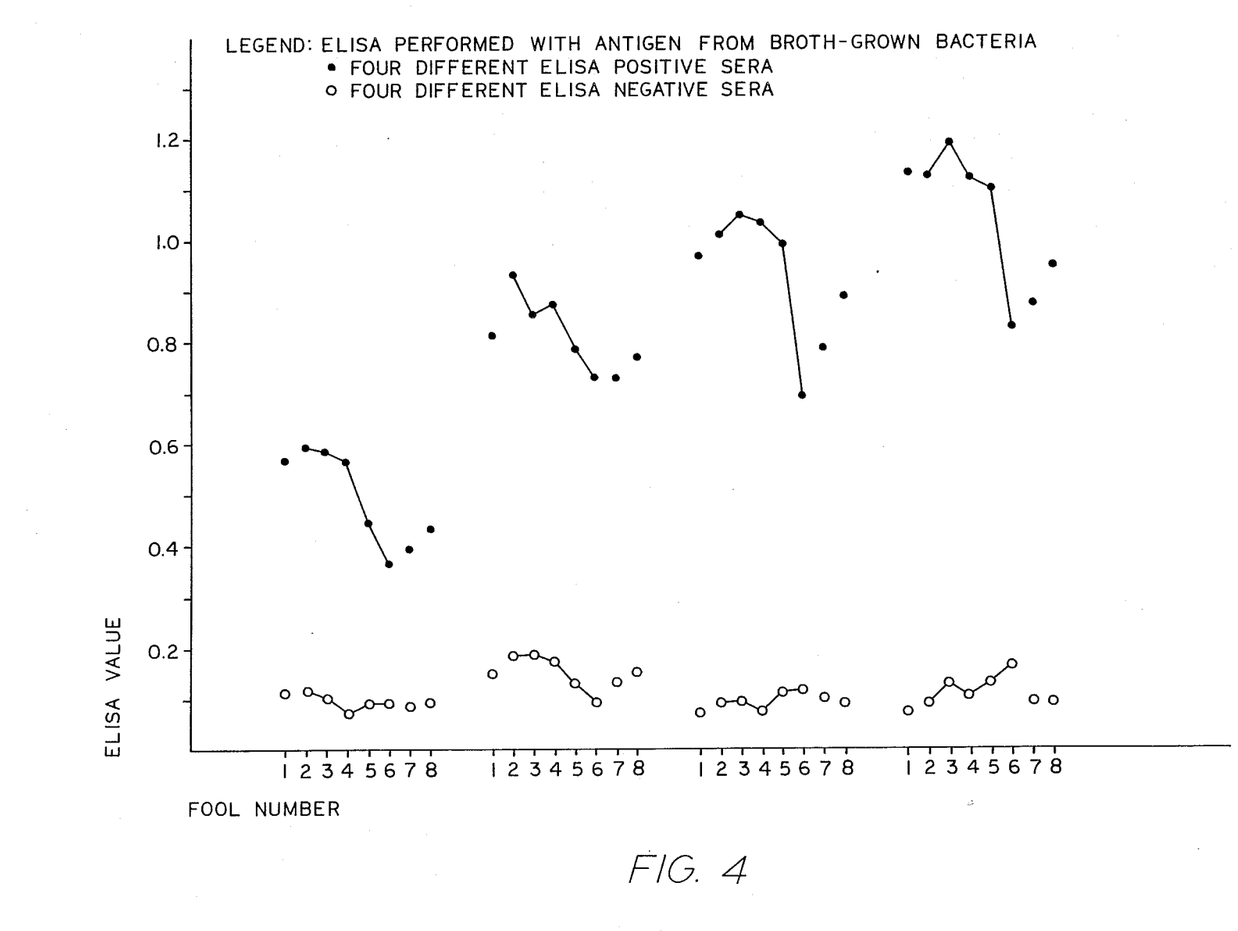
FIG. 4 compares four different positive and negative sera using an ELISA assay with antigen from both grown bacteria to detect *C. pylori*.

The antigenic activity of the individual protein fractions is shown in FIGS. 2–4. HM-CAP fractions were selected and pooled on the basis of urease activity and used as antigen in an ELISA assay. These antigens were extremely effective in detecting the presence, or absence, of anti-C. pylori serum IgG antibody. The presence or absence of the organism correlated with the presence or absence of the antigen. This correlation was confirmed by detecting the C. pylori organism with other less convenient but recognized methods. Two batches of C. pylori were grown, one using the plate method and one using the broth method, to determine (1) how much of this specificity could be accounted for by antigens other than urease and (2) whether the method of growth of the bacteria (plates versus liquid media, or broth) for antigen production has any effect on the specificity of the ELISA. Crude HM-CAP was prepared from both batches of bacteria and individually passed through the same agarose A-5m column. The elution diagrams are shown in FIG. 2.

In both cases two or more column fractions were pooled together to create the eight different pools designated in FIG. 2. Protein determinations were performed on each pool so that microtiter plates could be coated with an equivalent amount of protein (100 microliters of antigen at 0.007 mg protein per ml) from each of the pools. The protein determination can be seen in the following table.

| Pool Number | Fractions Pooled | Mg/Ml Protein Broth | Mg/Ml Protein Plate |
|---|---|---|---|
| 1 | 53–58 | 0.28 | 0.16 |
| 2 | 55–56 | 0.38 | 0.19 |
| 3 | 57–58 | 0.26 | 0.16 |
| 4 | 59–60 | 0.22 | 0.14 |
| 5 | 61–62 | 0.24 | 0.20 |
| 6 | 63–64 | 0.20 | 0.15 |
| 7 | 59–64 | 0.28 | 0.24 |
| 8 | 53–64 | 0.28 | 0.20 |

Pool 2 is equivalent to the HM-CAP antigen preparation used in the standardized assay. Four ELISA-positive and four ELISA-negative serum samples were selected at random and used to perform the ELISA assays. The results are shown in FIGS. 3 and 4.

Examination of FIGS. 3 and 4 demonstrate that Pools 1–4, representing agarose fractions 53–60, provide the greatest differentiation between ELISA-positive and ELISA-negative sera, as compared to pools 5–8. Pools 5–8 show some selectivity as test antigens and thus suggest that it is not necessary to further purify HM-CAP in order to have a C. pylori-specific ELISA assay.

These results indicate that the selection of the urease-positive column fractions for use as HM-CAP antigens in the C. pylori-specific ELISA assay provides adequate sensitivity and selectivity. Therefore, further separation into specific components is not necessary. Additionally, plate-grown and broth-grown bacteria are equally useful as the source of HM-CAP for ELISA antigens. The larger yield of urease protein in the broth-grown batch of HM-CAP (see FIG. 2) most likely accounts for the fact that pools 5–8 of the broth-grown antigen performed better than pools 5–8 of the plate-grown antigen due to less efficient separation of the two major peaks.

Thus FIGS. 3 & 4 show that the mixture of at least two proteins is just as effective in detecting C. pylori antibodies in serum as each protein individually. Although these data show that the higher molecular weight component, coinciding with urease activity, is a better antigen than the lower weight antigen they also suggest that the mixture is as good if not better in determining C. pylori infection. Thus, although the proteins can be further purified into individual components, stopping the purification prior to the separation of the mixture is sufficient.

A variety of methods can be used to detect C. pylori antibody in the serum. One skilled in the art will readily recognize that enzyme-linked immunosorbent assays (ELISA), radioimmuno assays (RIA), complement fixation, latex bead agglutination, immunoblot assays, and passive inmugglutination can all be used. In a preferred embodiment, the serological assay involves the ELISA method. This assay includes immobilizing the HM-CAP antigen on a solid phase support. After the antigen has been immobilized a serum sample to be tested is combined with the immobilized antigen and they are incubated for about 90 minutes at room temperature and under humid conditions. An antigen-antibody complex forms during the incubation. After the antigen antibody-complex is formed, alkaline-phosphatase-conjugated anti-human IgG is added to the antigen-antibody complex on the solid phase support and incubated for approximately 90 minutes, at room temperature under humid conditions to form an antigen-antibody-alkaline-phosphatase-conjugated anti-human IgG complex. A variety of substrates can be used to determine the amount of binding which has taken place. In a preferred embodiment, para-nitrophenyl phosphate is added to this complex and the resulting yellow product is measured to determine the amount of antigen-antibody complex formed, and thus the amount of antibody present in the serum. The above mentioned assay methods can also be used to monitor the treatment of *C. pylori* infection by collecting serial serum samples from treated subjects and performing said methods on each sample.

EXAMPLE 1

ELISA technique: Coat microtiter plate wells with 100 microliters of HM-CAP antigen diluted with PBS to approximately 0.007 milligrams per milliliter protein. In one embodiment a standard 96 well plate is used. After about 18 to 24 hours at 37° C. in a humid chamber, the antigen adheres to the plastic surface, forming a non-specific, permanent binding. The excess plastic protein-binding sites are blocked by incubating about 1% BSA (Bovine serum albumin) in PBS for about 30 minutes at approximately 37° C. in a humid chamber. The excess BSA is removed by washing three times with PBST (PBS Containing about 0.02% Tween-20). Next, about 100 microliters per well of serum is added in dilutions of either 1:50 or 1:100 in PBS. After incubation at room temperature, in a humid chamber for about 90 minutes, the excess antibodies are removed by washing three times with PBST. About 100 microliters per well of a calibration dilution of conjugate (goat anti-human IgG antibodies conjugated to the enzyme alkaline phosphatase) are added, and the mixture is incubated at room temperature in a humid chamber for about 90 minutes. After removing excess conjugate, i.e., unreacted conjugate, by washing three times with PBST, about 100 microliters per well of alkaline phosphatase substrate, for example para-nitrophenyl phosphate, are added. After additional incubation for about 60 minutes, in a humid chamber the yellow colored enzyme product is measured. For each microtiter plate includes a number of controls, for example, known ELISA-positive serum, known ELISA-negative serum and reaction blank. An optical density value of about 0.200 or higher is a positive result. The following results were observed:

| DIAGNOSIS OF C. PYLORI INFECTION | | |
|---|---|---|
| | + | − |
| HM-CAP ELSIA + | 113 | 3 |
| − | 3 | 90 |

*C. pylori* infection was diagnosed as either positive or negative by histological examination and culture of biopsy material, or by the $^{13}$C urea breath test.

The HM-CAP ELISA assay detected 113 of the 116 samples from individuals with *C. pylori* infection. This is a specificity of 97.4%. The sensitivity of the assay is determined by looking at the negative HM-CAP ELISA result. The results show 90 of 93 *C. pylori* negative individuals were detected. This is a sensitivity of 96.8%. The overall reliability of the test is 97.1% (203 out of 209 samples were accurately predicted). These data strongly indicate that there are few, if any, misclassifications using the ELISA assay.

EXAMPLE 2

KIT: A kit is prepared by incubating the HM-CAP antigen on a solid phase support. The solid phase support can be any charged membrane or plastic material. The solid phase support-antigen complex can then be packaged individually or in multiple combinations. The kit can also include controls for false positives and false negatives, and reagents. The kit can be used to detect 1 sample or multiple samples.

EXAMPLE 3

Latex agglutination assay: Antibodies against *C. pylori* can be measured in serum samples with HM-CAP coated latex bead particles. Additionally, the presence of antigens can be measured by coating the latex particles with monospecific antibody (anti-HM-CAP). Particles of polyvinyl or toluene latex of about 0.77 micron diameter or polystyrene latex particles (beads) measuring about 0.81 to 1.77 microns can be coated with HM-CAP. About 2.0 ml of the latex particles are suspended in approximately 20 ml of distilled water, mixed and filtered through a Whatman No. 40 filter paper. After adjusting the filtrate to about 2.0 optical density at a wavelength of 640 nm in phosphate-buffered saline, pH about 7.2., or equivalent buffer, about 0.1 ml of the latex suspension is diluted with about 5.0 ml of PBS. About 0.5 ml of a 0.5% antigen solution is added to the diluted latex suspension. This mixture is then incubated at about 37° C. for 30 minutes. The latex particles are then washed twice, each time with ten volumes of PBS. The final suspension is adjusted to an optical density of 0.3 using 0.1M glycine buffer containing 0.1% bovine serum albumin. In the assay equal volumes of coated latex particles and serum dilutions in 0.1M glycine buffer are mixed. Control tubes receive saline instead of serum. Tubes are incubated at 50° C. for 2 hours, centrifuged at 15,000×g for 3 minutes and gently tapped. The degree of clumping is noted. Clumping is due to the aggregation (agglutination) of the beads via the antigen-antibody complex formation.

EXAMPLE 4

Radiommunoassay: A 96-well microtiter plate is coated with about 100 microliters of an optimum concentration of antigen. After incubation at about 37° C. for about 18-24 hours, the excess binding sites in the wells are blocked with 1% BSA in PBS, or equivalent. About 100 microliters per well of appropriate dilution(s) of serum to be tested are added to duplicate wells and incubated at room temperature for about 2 hours. After washing the plates numerous times with PBST, 100 microliters per well of optimal dilution of goat or rabbit anti-human IgG, which has been labeled with 125-iodine, is added. The microliter plates are incubated for about 4 hours at room temperature, washed numerous times with PBST and air dried. The wells are counted in a gamma counter to determine the amount of radioactivity remaining in each well at the end of the test. Positive and negative sera are included on each plate as controls. The procedure is standardized to determine which values differentiate between a positive and a negative serum.

One skilled in the art will really appreciate the present invention is well adapted to carry out the objects and obtain the ends and advantages mentioned, as well as, those inherent therein. The methods, procedures and techniques described herein are presently representative of the preferred embodiments, are intended to be exemplary, and are not intended as limitations on the scope. Changes therein and other uses will occur to those skilled in the art which are encompassed within the spirit of the invention or defined by the scope of the appended claims.

What is claimed is:

1. A composition comprising substantially purified antigens from the high molecular weight cell-associated proteins of *Campylobacter pylori*, said antigens:

having a molecular weight of about 300,000 to 700,000 daltons as determined by agarose A-5 m column;

having a PI on isoelectric focusing of about 5.9 to 6.3;

having urease activity being soluble in PBS and Tris-chloride buffers;

being derived from the outer surface of the membrane of *Campylobacter pylori*; and being solubilized from the outer surface of the membrane with n-octyl-glucoside.

2. A serological assay for the detection of *Campylobacter pylori* infection, comprising, combining the antigens of claim 1 with a serum sample to be tested according to a method selected from the group consisting of enzyme-linked immunosorbent assay, radioimmunoassay, complement fixation, indirect hemagglutination and latex agglutination wherein measurement of an antigen-antibody complex is proportional to the amount of *Campylobacter pylori* in the serum sample.

3. The serological assay of claim 2, wherein said method is the enzyme-linked immunosorbent assay, which includes the steps of:

adding serum sample to an antigen immobilized on a solid phase support;

incubating the mixture of serum sample and immobilized support to form an antigen-antibody complex;

adding enzyme-conjugated anti-human IgG to said antigen-antibody complex;

incubating the antigen-antibody complex and enzyme-conjugated anti-human IgG mixture to form an antigen-antibody-enzyme-conjugated anti-human IgG complex;

adding substrate to the antigen-antibody-enzyme-conjugated anti-human IgG complex; and measuring the product or the change in the substrate to determine the amount of said antibody; wherein the product or change in the substrate measured is proportional to the amount of *Campylobacter pylori* in the serum sample.

4. The serological assay of claim 3, wherein the enzyme is selected from the group consisting of alkaline phosphatase, horseradish peroxidase and beta galactosidase.

5. A method of monitoring the treatment of *Campylobacter pylori* infection, comprising, collecting serial serum samples from the treated subject and repeating the steps of claim 3 on each sample.

6. The serological assay of claim 2, wherein said method is the radioimmunoassay, which includes the steps of:

adding serum sample to a well coated with antigen;

incubating said serum sample in said coated well to form an antigen-antibody complex;

adding radioactive labeled anti-human IgG;

incubating the mixture of the antigen-antibody complex and anti-human IgG to form an antigen-antibody-anti-human IgG complex; and measuring the amount of radioactivity bound in the antigen-antibody-anti-human IgG complex; wherein the amount of radioactivity bound is proportional to the amount of *Campylobacter pylori* in the serum sample.

7. The serological assay of claim 2, wherein said method is latex agglutination, which includes the steps of:

adding serum sample to latex beads coated with antigen;

incubating the serum sample and coated latex beads; and measuring the degree of clumping; wherein the degree of clumping is proportional to the amount of *Campylobacter pylori* in the serum sample.

8. A kit for determining the presence of *Campylpbacter pylori* antibody, comprising, a container having the antigens of claim 1 immobilized on a solid phase support.

9. The kit of claim 8, further comprising, false negative controls and a control having false positive controls.

* * * * *

UNITED STATES PATENT OFFICE
CERTIFICATE OF CORRECTION

Patent No. 4,882,271      Dated November 21, 1989

Inventor(s) Dolores G. Evans; Doyle J. Evans; David Y. Graham

It is certified that error appears in the above-identified patent and that said Letters Patent is hereby corrected as shown below:

Column 1, line 48, after "of 20,000 to" add -- 100,000 daltons which were unique to C. pylori. However, --

Column 9, line 24, after "activity" add -- ; --

Column 10, line 47, after "comprising," add -- a container having --

Column 10, line 48, after "and" delete "a control having".

Signed and Sealed this

Second Day of October, 1990

Attest:

HARRY F. MANBECK, JR.

Attesting Officer      Commissioner of Patents and Trademarks